(12) United States Patent
Turkowitz

(10) Patent No.: US 7,666,859 B2
(45) Date of Patent: Feb. 23, 2010

(54) SKIN COMPOSITIONS CONTAINING HYDROCORTISONE

(76) Inventor: Norman Turkowitz, 57 W. 57th St. - Suite 800, New York, NY (US) 10019

( * ) Notice: Subject to any disclaimer, the term of this patent is extended or adjusted under 35 U.S.C. 154(b) by 112 days.

(21) Appl. No.: 11/899,600

(22) Filed: Sep. 6, 2007

(65) Prior Publication Data

US 2008/0063614 A1 Mar. 13, 2008

Related U.S. Application Data

(60) Provisional application No. 60/843,216, filed on Sep. 8, 2006.

(51) Int. Cl.
- *A61K 31/56* (2006.01)
- *A61K 31/04* (2006.01)
- *A61Q 1/04* (2006.01)
- *A61P 17/16* (2006.01)
- *A01N 43/50* (2006.01)

(52) U.S. Cl. ........................ 514/171; 514/179; 514/390; 424/64

(58) Field of Classification Search .................. 424/59, 424/64; 514/171, 179, 390
See application file for complete search history.

(56) References Cited

U.S. PATENT DOCUMENTS

| | | | |
|---|---|---|---|
| 4,678,663 A | 7/1987 | Scott et al. | |
| 4,725,429 A | 2/1988 | Scott et al. | |
| 4,738,956 A | 4/1988 | Scott et al. | |
| 4,935,228 A | 6/1990 | Finkenaur et al. | |
| 5,747,017 A | 5/1998 | Nichols et al. | |
| 5,962,000 A * | 10/1999 | Yanagida et al. | 424/401 |
| 6,001,374 A | 12/1999 | Nichols | |
| 6,027,739 A | 2/2000 | Nichols | |
| 6,203,809 B1 | 3/2001 | Nichols | |
| 6,224,888 B1 | 5/2001 | Vatter et al. | |
| 6,228,351 B1 | 5/2001 | Viders | |
| 6,309,657 B2 | 10/2001 | Vatter et al. | |
| 6,329,413 B1 * | 12/2001 | Farber | 514/390 |
| 6,395,263 B1 | 5/2002 | Nichols et al. | |
| 6,455,055 B1 | 9/2002 | Walling et al. | |
| 6,509,009 B2 | 1/2003 | Nichols et al. | |
| 6,528,071 B2 | 3/2003 | Vatter et al. | |
| 6,713,075 B2 | 3/2004 | Bekele | |
| 7,030,203 B2 | 4/2006 | Mosbey et al. | |
| 7,037,511 B1 | 5/2006 | Gers-Barlag et al. | |
| 2001/0003586 A1 | 6/2001 | Vatter et al. | |
| 2001/0033850 A1 | 10/2001 | Vatter et al. | |
| 2002/0197221 A1 | 12/2002 | Nichols et al. | |
| 2003/0003066 A1 | 1/2003 | Nichols et al. | |
| 2003/0118621 A1 | 6/2003 | Heidenfelder et al. | |
| 2004/0228821 A1 | 11/2004 | Sunkel et al. | |
| 2004/0231070 A1 | 11/2004 | Morrissey et al. | |
| 2004/0258721 A1 | 12/2004 | Bauer et al. | |
| 2005/0008667 A1 | 1/2005 | Liechty et al. | |
| 2005/0014674 A1 | 1/2005 | Liechty et al. | |
| 2005/0036960 A1 * | 2/2005 | Bussey et al. | 424/59 |
| 2006/0008489 A1 | 1/2006 | Egawa et al. | |
| 2006/0034798 A1 | 2/2006 | Mosbey et al. | |
| 2006/0110415 A1 | 5/2006 | Gupta | |

FOREIGN PATENT DOCUMENTS

JP 11209291 A 8/1999

OTHER PUBLICATIONS

Honey PDF [online], Centerchem, Inc., Oct. 1998 [retrieved Oct. 24, 2008], Retrieved from Internet (URL-http://www.centerchem.com/PDFs/Honey%20Ext%20tech%20doc.pdf).*
WWW.AMAZON.COM, LIP-INK Tinted Waxless Lip Balm Tropical Violet Collection (3 Pack), dated Jun. 12, 2006.
WWW.AMAZON.COM, LIP-INK Shine Moisturizer Vial—.25 fl.oz., dated Jun. 12, 2006.

* cited by examiner

*Primary Examiner*—Johann R Richter
*Assistant Examiner*—Andriae M Holt
(74) *Attorney, Agent, or Firm*—Onofrio Law; Dara L. Onofrio, Esq

(57) ABSTRACT

Skin compositions comprising, hydrocortisone; allantoin; and a water-based vehicle that is essentially free of petroleum jelly, mineral oil and wax; and related method for protecting, healing and/or soothing the skin comprising: applying an effective amount of a cosmetic preparation selected from the group consisting of hand cream, foot cream, body cream, lip cream, lip gloss, lip stick, gel, balm and lotion to the skin surface; wherein said cosmetic preparation includes a skin composition made of hydrocortisone; allantoin; and a water-based vehicle that is essentially free of petroleum jelly, mineral oil and wax; and said effective amount is enough to protect, heal and/or soothe the skin surface.

17 Claims, No Drawings

SKIN COMPOSITIONS CONTAINING HYDROCORTISONE

This application claims the benefit of U.S. provisional application No. 60/843,216 filed Sep. 8, 2006, which is incorporated herein in its entirety by reference.

FIELD OF THE INVENTION

The present invention relates to topical water-based skin compositions containing hydrocortisone and allantoin. In particular, the invention compositions do not contain any petroleum jelly or mineral oil and are essentially wax free.

BACKGROUND OF THE INVENTION

Skin in general is composed of three distinct layers: the outer protective stratum corneum; the middle epidermis layer and the inner dermis layer. Sweat glands and hair roots are found in the dermis layer.

Lips are a type of skin. They are the two fleshy folds which surround the opening of the mouth in humans and many other vertebrates, and in humans are organs of speech essential to certain articulations. The pinkish or reddish margin of a human lip is composed of non glandular mucous membrane and is usually exposed when the mouth takes on its natural set.

Millions of people suffer from dry chapped lips each winter. The reason can be found in the structure of lips themselves. The lips' exposed mucous membrane structure is actually different than other skin. Unlike skin, lips do not have the same protective outer layer, or stratum corneum. Nor do lips have the same complement of oil and sweat glands found in other skin. Sweat glands add moisture to skin, but the lips' only source of moisture is saliva inside the mouth. Thus, harsh winter, wind, cold, sun and dryness—indoors and outdoors—make lips a vulnerable target for chapping. Various cosmetic products have been developed to aid in combating this problem.

In general, cosmetic and/or dermatological compositions are relatively well known and typically contain petroleum jelly, mineral oil and wax or a combination of these ingredients.

Representative patents and publications that relate to the general disclosure of cosmetic compositions containing ingredients such as alcohols, oils, saturated fatty acids, vitamins, etc. include U.S. Pat. No. 7,037,511 B1 to Gers-Barlag et al; U.S. Pat. No. 7,030,203 B2 to Mosbey et al.; U.S. Pat. No. 6,455,055 B1 to Walling et al.; U.S. Pat. Nos. 6,309,657 B2 and 6,224,888 B1 to Vatter et al.; U.S. Pat. No. 4,935,228 to Frinkenaur et al.; U.S. Pat. Nos. 4,725,429 and 4,678,663 to Scott et al.; U.S. Publication No. 2006/0110415 A1 to Gupta; U.S. Publication No. 2006/0034798 A1 to Mosbey et al.; U.S. Publication Nos. 2005/0014674 A1 and 2005/0008667 A1 to Liechty et al.; U.S. Publication No. 2006/0008489 A1 to Egawa et al.; U.S. Publication No. 2004/0258721 A1 to Bauer et al.; U.S. Publication No. 2004/0231070 A1 to Morrissey et al.; U.S. Publication No. 2004/0228821 A1 to Sunket et al.; U.S. Publication No. 2003/0118621 A1 to Heidenfelder et al.; and U.S. Publication Nos. 2001/0033850 A1 and 2001/0003586 A1 to Vatter et al.

Other known cosmetic compositions are described in U.S. Pat. No. 6,713,075 B2 to Bekele; U.S. Pat. No. 6,528,071 B2 to Vatter et al.; U.S. Pat. No. 6,228,351 to Viders; and U.S. Pat. No. 4,738,956 to Scott et al. In particular the Nichols patents and publications define smear resistant lip cosmetics that are said to contain no wax or petroleum jelly. See U.S. Pat. Nos. 6,509,009; 6,395,263; 6,203,809; 6,027,739; 6,001,374; 5,747,017 and U.S. Publications 2003/0003066 A1 and 2002/0197221 A1. However, these references do not contain either hydrocortisone or allantoin which are essential ingredients in the invention compositions.

It is well known that wax and related substances when applied to the skin surface, especially the lips, dry out rather than moisten the skin. The invention compositions have been formulated to be virtually waxless to moisten the skin surface and to provide no wax buildup. The compositions are also found to soothe and heal irritated or itchy skin surfaces.

It is therefore a general object of the invention to provide skin compositions made of a water-based vehicle essentially free of petroleum jelly, mineral oil and wax containing both hydrocortisone and allantoin. Advantageously over known compositions the present invention absorbs directly into the skin tissue and provides a moisturizer for the skin surface.

A specific object of the invention is to provide a lip composition that absorbs directly into the lip tissue and provides a moisturizer for the lip surface.

Another object of the invention is use of the composition in cosmetic preparations including creams, balms, lotions, gels, glosses or stick forms for application to skin tissue surfaces.

A specific object of the invention is to use as a lip healer for chapped red and sore lips and helps prevent further chapping.

Another object is to provide a multi-purpose composition for protecting the skin.

Yet another object of the invention is to provide a multi-purpose composition for healing the skin.

Still another object of the invention is to provide a multi-purpose composition for soothing irritated or itchy skin.

Another object of the invention is to provide body, hand and foot creams, lotions and gels for protecting, healing and/or soothing the skin.

Another object of the invention is to provide a lip composition which aids in healing cold sores as well as sores caused by the herpes simplex virus.

Still another object of the invention is to provide a skin composition which aids in preventing, alleviating and/or hiding wrinkles and scars.

Another specific object of the invention is to provide a skin composition which contains sun screen materials to protect the skin.

Another specific object of the invention is to provide a method for protecting, healing and/or soothing the skin by topically applying an effective amount of the invention skin composition to protect, heal and/or soothe the skin surface.

SUMMARY OF THE INVENTION

In the present invention, these purposes, as well as others which will be apparent, are achieved generally by providing a skin composition comprising: hydrocortisone; allantoin; and a water-based vehicle that is essentially free of petroleum jelly, mineral oil and wax.

The hydrocortisone is present in an amount up to 0.1% by weight.

The allantoin is present, preferably, in an amount up to 0.5% by weight.

The water-based vehicle is up to 80% by weight water. The water-base vehicle may include additional materials such as alcohols, oils, saturated fatty acids and esters.

The alcohols used in the composition are water-soluble. Preferred alcohols include octyldodecanol, cetyl alcohol, and stereth-20. The alcohol component is a good filler material and is easily absorbed and blends with the base material.

The composition may further include *butyrospermum parkii* shea butter and honey.

The oil in the composition is preferably *simmondsia chinensis* (jojoba) seed oil, emu oil and hydrogenated olive oil.

The composition may also contain vitamins. The preferred vitamins are vitamin A, vitamin B, vitamin C and vitamin E.

Further materials which may be included in the composition are caprylic/capric triglycerides; hydrogenated polyisobutene; garcinia indica seed butter; sorbitol, sorbitan olivate; glyceryl stearate; PEG-100 stearate; sodium carbomer; butylene glycol; saccharomyces/magnesium ferment; disodium EDTA; phospholipids; sphingolipids; hyaluronic acid, sodium hyaluronate; tocepheryl acetate; retinyl palmitate; ascorbyl palmitate; phenoxyethanol; methylparaben; ethylparaben; butylparaben; propylparaben; isobutylparaben; and flavors.

In preferred embodiments for applications to the lips, the composition may also include color pigments depending on the desired color as well as various flavors.

The invention compositions are used in conventional cosmetic preparations to produce creams, lotions, gels and balms for hand, body, foot and lip applications. Specific lip products include lip creams, lip balms, lip glosses, lip lotions and lip sticks.

Other objects, features and advantages of the present invention will be apparent when the detailed description of the preferred embodiments of the invention are considered.

DETAILED DESCRIPTION OF THE INVENTION

In general, the invention provides skin compositions comprising: hydrocortisone; allantoin; and a water-based vehicle that is essentially free of petroleum jelly, mineral oil and wax.

The hydrocortisone is present in an amount up to 0.1% by weight.

Hydrocortisone is a synthetic cortisol and is typically used as a drug to fight allergies and inflammation. Known topical applications are for its anti-inflammatory effect in allergic rashes, eczema and certain other inflammatory conditions. In the present invention compositions the hydrocortisone, in combination with the other composition ingredients provides a medicinal effect to moisturize and smooth the skin surface. The chemical formula is $C_{21}H_{30}O_5$ and has a molecular weight of 362.465 g/mol.

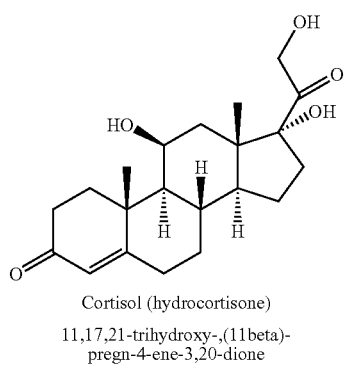

Cortisol (hydrocortisone)
11,17,21-trihydroxy-,(11beta)-
pregn-4-ene-3,20-dione

The allantoin is present, preferably, in an amount up to 0.5% by weight.

Allantoin is a botanical extract of the comfrey plant and is used for its healing, soothing and anti-irritating properties. Allantoin is known to help heal wounds and skin irritations and can stimulate growth of healthy tissue. The chemical formula is $C_4H_6N_4O_3$ and has a molecular weight of 158.1164 g/mol. It is also called 5-ureidohydantoin, glyoxyldiureide and 5-ureidohydantoin. It's a product of oxidation of uric acid. The keratolytic effect and abrasive and astringent properties of allantoin make it suitable for use in skin softening cosmetic preparations.

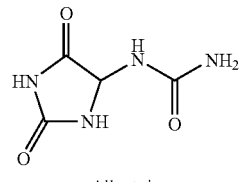

Allantoin
Chemical name
(2,5-Dioxo-4-imidazolidinyl) urea

The water based vehicle is up to 80% by weight water. The water-base vehicle may include additional materials such as alcohols, oils, saturated fatty acids and esters.

The alcohols used in the composition are water-soluble. Preferred alcohols include octyldodecanol, cetyl alcohol, and stereth-20. The alcohol component is a good filler material and is easily absorbed and blends with the base material.

The composition may further include *butyrospermum parkii* shea butter and honey. Shea butter, commonly known as Karité is derived from the Shea Nut Tree (*butyrospermum parkii*) which grows in the western region of Africa. The fruits of these trees contain a nut which is dried and ground. The powder is boiled in water to release an unctuous substance which rises to the top and solidifies to create Shea Butter (Diop). The butter is used in the compositions to help moisturize and protect the skin from sun, wind, heat and salt water. Shea butter cannot rob the skin of its natural oils and can actually help stimulate collagen production. As such, it is effective in helping to alleviate wrinkles, scars and burns.

The oil in the composition is preferably simmondsia chinensis (jojoba) seed oil, emu oil and hydrogenated olive oil

*Simmondsia chinensis* (jojoba) seed oil is quite similar to the skin's own chemical composition called sebum. When applied to the skin, the oil combines with the sebum and helps it clear the skin of impurities.

Emu oil contains natural anti-inflammatory, healing properties with a wide range of omega oils that are known to facilitate good health. It contains a complete source of essential fatty acids, which are fats that humans cannot manufacture or synthesize, they must be obtained from diet. This oil contains omega 3, 6, 9 essential fatty acids and is considered a powerful skin moisturizer and possess strong anti-inflammatory properties.

The composition may also contain vitamins. The preferred vitamins are vitamin A, vitamin B, vitamin C and vitamin E, although other vitamins can be substituted and used in the compositions.

Further materials which may be included in the composition are caprylic/capric triglycerides; hydrogenated polyisobutene; garcinia indica seed butter; sorbitol, sorbitan olivate; glyceryl stearate; PEG-100 stearate; sodium carbomer; butylene glycol; saccharomyces/magnesium ferment; disodium EDTA; phospholipids; sphingolipids; hyaluronic acid, sodium hyaluronate; tocepheryl acetate; retinyl palmitate; ascorbyl palmitate; phenoxyethanol; methylparaben; ethylparaben; butylparaben; propylparaben; isobutylparaben.

Hyaluronan or hyaluronic acid or hyaluronate is a glycosaminoglycan distributed widely throughout connective, epithelial and neural tissues and is found in many tissues of the body such as skin, cartilage and the vitreous humor. It is one of the chief components of the extracellular matrix, contributes significantly to cell proliferation and migration. Due to its moisturizing effects hyaluronan is a good skin care ingredient. Injections of hyaluronan have been used for filling soft tissue defects such as facial wrinkles and are analogous to collagen injections but have the advantages of longer lasting effects and decreased risk of allergic reaction.

Disodium EDTA (ethylene diamine tetra acetic acid) commonly referred to as EDTA is a stabilizer in cosmetic products that is a chelating compound. The function of a chelating compound is to prevent ingredients from binding to any trace elements that may be present. If mineral trace elements bind with other ingredients, unwanted changes in the product may occur that could influence the texture, consistency or even the smell of the product. This ingredient is provided for more stability and can be used as a viscosity adjuster.

In preferred embodiments for application to the lips the composition may also include color pigments depending on the desired color.

Generally FD&C colours are used in the invention compositions and are approved for use in food, drugs and cosmetics. D&C colours are also approved for use in drugs and cosmetics and may be used in the invention compositions. Colours can be blended to yield different shades. The INC abbreviated names for FD&C colours are as follows:

Black Colour—Red 40, Blue 1, Yellow 5

Dark Blue Colour—Blue 1

Sky Blue Colour—Blue 1

Green Colour—Yellow 5, Blue 1

Orange Colour—Yellow 6

Peach Colour—Yellow 5, Yellow 6

Pink Colour—Red 3

Purple Colour—Red 40, Blue 1

Teal Green Colour—Green 5

Yellow Colour—Yellow 5

The invention compositions can be made to taste like a variety of different flavors. Typically, natural and artificial flavors are in an oil soluble (vegetable oil) base. Edible flavours can be combined with a sweetener to bring out the full flavor. Flavors can include, but are not limited to, blackberry, cherry, mocha latte, green apple, mango papaya, maple sugar, fresh peach, coconut, ripe raspberries, strawberry, vanilla cream, butterscotch, black cherry, chocolate, coffee, mango, pina colada, vanilla and more.

The invention composition for application to the lip can comprise:

hydrocortisone, which is present in the composition in an amount greater than 0%, up to 0.1% by weight;

allantoin, which is present in the composition in an amount greater than 0%, up to 1% by weight;

a water based vehicle that is free of petroleum jelly, mineral oil and wax, wherein said vehicle includes emu oil; and at least one of the materials selected from the group consisting of color pigments and flavors;

wherein the hydrocortisone and allantoin are present in amounts effective to protect, heal and/or soothe the lip surface.

The present invention will be illustrated in more detail by the following examples without limiting the scope of the claimed process and formulations in any way.

EXAMPLE 1

A lip balm with vanilla mint flavor was made according to the following formulation:

Formula 1

13.4% by weight—Water-based vehicle: octyldodecanol, cetyl alcohol, steareth-20, caprylic/capric triglycerides, hydrogenated polyisobutene, simmondsia chinensis (jojoba) seed oil, emu oil, sorbitol, sorbitan olivate, hydrogenated olive oil, glyceryl stearate, PEG-100 stearate, sodium carbomer, butylene glycol, saccharomyces/magnesium ferment, sodium hyaluronate, tocopheryl acetate, retinyl palmitate, ascorbyl palmitate, phenoxyethanol, methylparaben, ethylparaben, butylparaben, propylparaben, and isobutylparaben;

4.9% by weight—Additional ingredients: butyrospermum parkii (shea butter), garcinia indica seed butter, disodium EDTA, honey, phospholipids, sphingolipids;

0.1% by weight—Hydrocortisone;

0.5% by weight—Allantoin;

1.0% by weight—Flavor: Vanilla Mint Flavor;

The remaining ingredient in the formulation is water (up to 80 weight %).

The composition is solidified to produce the balm.

EXAMPLE 2

A lip balm with vanilla mint flavor was made according to the following formulation:

Formula 2

13.4% by weight—Water-based vehicle: Octyldodecanol, cetyl alcohol, steareth-20, caprylic/capric triglycerides, hydrogenated polyisobutene, *simmondsia chinensis* (jojoba) seed oil, emu oil, sorbitol, sorbitan olivate, hydrogenated olive oil, glyceryl stearate, PEG-100 stearate, sodium carbomer, butylene glycol, saccharomyces/magnesium ferment, hyaluronic acid, tocopheryl acetate, retinyl palmitate (Vita—vitamine supplement $C_{36}H_{60}O_2$), ascorbyl palmitate, phenoxyethanol, methylparaben, ethylparaben, butylparaben, propylparaben, and isobutylparaben;

4.9% by weight—Additional ingredients: *butyrospermum parkii* (shea butter), garcinia indica seed butter, disodium EDTA, honey, phospholipids, sphingolipids, 0.1% by weight—Hydrocortisone;

0.5% by weight—Allantoin;

1.0% by weight Flavor: Vanilla Mint Flavor;

The remaining ingredient in the formulation is water (up to 80 weight %).

The composition is solidified to produce the balm. Although Vita is used in this example other vitamins can be substituted and used in the formulation therein.

EXAMPLE 3

A lip composition was made according to the following formulation:

Formula 3

13.4% by weight—Water-based vehicle: Octyldodecanol, cetyl alcohol, steareth-20, caprylic/capric triglycerides, hydrogenated polyisobutene, *simmondsia chinensis* (jojoba) seed oil, emu oil, sorbitol, sorbitan olivate, hydrogenated olive oil, glyceryl stearate, PEG-100 stearate, sodium carbomer, butylene glycol, saccharomyces/magnesium ferment, hyaluronic acid, tocopheryl acetate, retinyl palmitate (Vita—vitamine supplement $C_{36}H_{60}O_2$), ascorbyl palmitate, phenoxyethanol, methylparaben, ethylparaben, butylparaben, propylparaben, and isobutylparaben;

4.9% by weight—Additional ingredients: butyrospermum parkii (shea butter), garcinia indica seed butter, disodium EDTA, honey, phospholipids, sphingolipids, 0.1% by weight—Hydrocortisone;

0.5% by weight—Allantoin;

The remaining ingredient in the formulation is water (up to 80 weight %).

Although Vita is used in this example other vitamins can be substituted and used in the formulation therein.

EXAMPLE 4

A lip composition was made according to the following formulation:

Formula 4

Up to 4 weight percent shea butter;

up to 7 weight percent of octyldodecanol and cetyl alcohol;

up to 4.5 weight percent of steareth-20, caprylic/capric triglycerides; hydrogenated polyisobutene and garcinia indica seed butter;

up to 2 weight percent of simmondsia chinensis (jojoba) seed oil, emu oil, sorbitol, sorbitan olivate; hydrogenated olive oil;

up to 0.7 weight percent of glyceryl stearate, PEG-100 stearate, sodium carbomer, butylene glycol, saccharomyces/magnesium ferment, disodium EDTA;

up to 1 percent by weight hydrocortisone;

up to 0.5 percent by weight allantoin;

up to 1.15 percent by weight of honey, phospholipids, sphingolipids, hyaluronic acid, sodium hyaluronate, tocepheryl acetate, retinyl palmitate, ascorbyl palmitate, phenoxyethanol, methylparaben, ethylparaben, butylparaben, propylparaben, isobutylparaben; and up to 1 percent by weight of flavor.

The remaining ingredient in the composition is water present up to 80 weight percent.

The lip compositions of Formulas 1 to 4 in the examples above were applied to the lips of test subjects. The compositions imparted moisture to the lips and provided a smooth lip surface. Over time the lip surface did not crack, as is typical in compositions including a wax component. Instead the lip surface remained smooth and retained the lip compositions longer which prevented the need for frequent reapplications.

EXAMPLE 5

A skin composition was made according to the following formulation:

Formula 5

13.4% by weight—Water-based vehicle: Octyldodecanol, cetyl alcohol, steareth-20, caprylic/capric triglycerides, hydrogenated polyisobutene, *simmondsia chinensis* (jojoba) seed oil, emu oil, sorbitol, sorbitan olivate, hydrogenated olive oil, glycelyl stearate, PEG-100 stearate, sodium carbomer, butylene glycol, saccharomyces/magnesium ferment, hyaluronic acid, tocopheryl acetate, retinyl palmitate (Vita—vitamine supplement $C_{36}H_{60}O_2$), ascorbyl palmitate, phenoxyethanol, methylparaben, ethylparaben, butylparaben, propylparaben, and isobutylparaben;

4.9% by weight—Additional ingredients: butyrospermum parkii (shea butter), garcinia indica seed butter, disodium EDTA, honey, phospholipids, sphingolipids, 0.1% by weight—Hydrocortisone;

0.5% by weight—Allantoin;

The remaining ingredient in the formulation is water (up to 80 weight %).

Although Vita is used in this example other vitamins can be substituted and used in the formulation therein.

The skin composition of Formula 5 are incorporated into cosmetic preparations selected from the group consisting of hand cream, foot cream, body cream, lip cream, lip gloss, lip stick, gel, balm and lotion and are topically applied to the skin surface in an effective amount to moisturize, protect, heal and/or soothe the skin surface.

The invention compositions are used to produce creams, balms, gels and lotions for use on hands, feet and the body. Lip creams, lip glosses, lip balms, lip lotions and lip sticks are preferred applications. These various applications vary in terms of viscosity of the material. For example, to make the lip balm the lip composition is solidified with an emulsifier.

Lip gloss can be provided in an array of colors and finishes. Lip gloss is distributed as a viscous liquid or a soft solid. It can be translucent (clear lip gloss can be layered over regular lipstick for extra shine) or various shades of opacity, including frosted, glittery and metallic looks. Gloss, like lipstick, can be applied different ways. The preferred way is a tube, which typically has a rounded or sloped application surface meant to contour to the lips. It can also be squeezed into one's finger and applied evenly. Other liquid glosses can come in cylindric containers, with a cosmetic wand used to apply the gloss. Soft solid glosses can come in pots and panels, which are used with fingers or a lipstick brush, or tubes, which are used like lipstick. The lip gloss of the invention is also used as a moisturizer.

Lip balms are substances topically applied to the lips of the mouth to relieve chapped or dry lips and cold sores. Typical balms are usually manufactured from beeswax, petroleum jelly, menthol, camphor, scented oils and various other ingredients. However, the invention balms are essentially free of petroleum jelly, mineral oil and wax. Vitamins, alum, salicylic acid or sun screen may be added to minimize sun damage. The lip balm may come in small containers, where a finger is used to spread it on the lips or in stick form (similar to lipstick) which is applied directly to the lips.

A preferred application of the invention composition is as a lip cream. The composition ingredients when combined form a cream-like composition without the addition of any additional materials. A thin layer is applied to the user's lips either directly from the tube, with the user's fingertips or with an applicator. Within 60 seconds the composition is absorbed into the lip surface. The single application generally lasts the entire day but a secondary application may be applied later in the day or evening. Typically, known lip creams, balms, lotions and sticks contain wax and are typically are applied to just seal the lips. Over time the lip becomes irritated and the material cracks off. These known materials act like a sealer. In contrast, the lip compositions of the invention do not provide a superficial application but are absorbed into the lip surface. The invention compositions also do not contain wax and therefore eliminate the irritation and cracking typically caused by the wax.

The invention also provides a method for protecting, healing and/or soothing the skin by applying an effective amount of a cosmetic preparation selected from the group consisting of hand cream, foot cream, body cream, lip cream, lip gloss, lip stick, gel, balm and lotion to the skin surface. The cosmetic preparation includes a skin composition made of hydrocortisone; allantoin; and a water-based vehicle that is essentially free of petroleum jelly, mineral oil and wax. The effective amount is enough to protect, heal and/or soothe the skin surface.

The invention compositions can be formulated to a variety of different colors, finishes and flavors depending on the desired result. The compositions are not limited to any particular color or flavor and are meant to encompass a number of varieties. The finishes can be cream, shimmer and gloss.

The foregoing description of various and preferred embodiments of the present invention has been provided for purposes of illustration only, and it is understood that numerous modifications, variations and alterations may be made without departing from the scope and spirit of the invention as set forth in the following claims.

What is claimed is:

1. A lip composition comprising:
   hydrocortisone, which is present in the composition in an amount greater than 0%, up to 0.1% by weight;
   allantoin, which is present in the composition in an amount greater than 0%, up to 1% by weight;
   a water based vehicle that is free of petroleum jelly, mineral oil and wax, wherein said vehicle includes emu oil; and
   at least one of the materials selected from the group consisting of color pigments and flavors;
   wherein the hydrocortisone and allantoin are present in amounts effective to protect, heal and/or soothe the lip surface.

2. The lip composition according to claim 1, further comprising a cosmetic preparation selected from the group consisting of cream, gloss, gel, balm, lotion and stick.

3. The lip composition according to claim 1 wherein said water-based vehicle is up to 80% by weight water.

4. The lip composition according to claim 1, further comprising shea butter.

5. The lip composition according to claim 1, wherein said water-base vehicle further includes at least one of the materials selected from the groups consisting of alcohols, oils, saturated fatty acids, esters.

6. The lip composition according to claim 5, wherein said alcohol is water-soluble.

7. The lip composition according to claim 6 wherein said alcohol is selected from the group consisting of octyldodecanol, cetyl alcohol, and stereth-20.

8. The lip composition according to claim 5, wherein said oil is selected from the group consisting of jojoba seed oil and olive oil.

9. The lip composition according to claim 1, further containing honey.

10. The lip composition according to claim 1, further containing vitamins.

11. The lip composition according to claim 10, wherein said vitamins are selected from the group consisting of vitamin A, vitamin B, vitamin C and vitamin E.

12. The lip composition according to claim 1, further including material selected from the group consisting of caprylic/capric triglycerides; hydrogenated poyisobutene; garcinia indica seed butter; sorbitol, sorbitan olivate; glyceryl stearate; PEG-100 stearate; sodium carbomer; butylene glycol; saccharomyces/magnesium ferment; disodium EDTA; phospholipids; sphingolipids; hyalluronic acid, sodium hyaluronate; tocepheryl acetate; retinyl palmitate; ascorbyl palmitate; phenoxyethanol; methylparaben; ethylparaben; butylparaben; propylparaben; isobutylparaben.

13. The lip composition according to claim 1, further containing a sun screen.

14. A cream using the lip composition according to claim 1.

15. A balm using the lip composition according to claim 1.

16. A lotion using the lip composition according to claim 1.

17. A method for protecting, healing and/or soothing the lip comprising:
   applying an effective amount of a cosmetic preparation selected from the group consisting of lip cream, lip gloss, lip stick, lip gel, lip balm and lip lotion to the lip surface;
   wherein said cosmetic preparation includes a lip composition made of hydrocortisone, which is present in the composition in an amount greater than 0%, up to 0.1% by weight;
   allantoin, which is present in the composition in an amount greater than 0%, up to 1% by weight; and
   a water-based vehicle that is free of petroleum jelly, mineral oil and wax, wherein said vehicle includes emu oil; and
   wherein the hydrocortisone and allantoin are present in amounts effective to protect, heal and/or soothe the lip surface.

* * * * *